(12) United States Patent
Alvhäll et al.

(10) Patent No.: US 6,518,434 B2
(45) Date of Patent: Feb. 11, 2003

(54) COUPLING PROCESS

(75) Inventors: Jörgen Alvhäll, Mölnbo (SE); Daniel Edvardsson, Södertälje (SE); Panagiotis Ioannidis, Spånga (SE); Magnus Sjögren, Stockholm (SE); Maria Szönyi, Uttran (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/806,149

(22) Filed: Mar. 28, 2001

(65) Prior Publication Data

US 2002/0128452 A1 Sep. 12, 2002

Related U.S. Application Data

(63) Continuation of application No. PCT/SE01/00177, filed on Jan. 30, 2001.

(30) Foreign Application Priority Data

Feb. 7, 2000 (SE) .............................................. 0000382

(51) Int. Cl.$^7$ .................... C07D 263/04; C07D 207/04; C07D 205/04
(52) U.S. Cl. ........................................ 548/215; 548/953
(58) Field of Search ................. 548/548, 953, 548/215

(56) References Cited

U.S. PATENT DOCUMENTS

| 4,686,295 A | 8/1987 | Youssefyeh et al. |
| 4,946,942 A | 8/1990 | Fuller et al. |
| 5,028,693 A | 7/1991 | Fuller et al. |
| 5,359,086 A | 10/1994 | Merslavic et al. .......... 548/533 |
| 5,610,297 A | 3/1997 | Powers |
| 6,265,397 B1 | 7/2001 | Karlsson et al. ....... 514/210.17 |

FOREIGN PATENT DOCUMENTS

| DE | 3 003 653 | 8/1981 |
| DE | 3 227 055 | 1/1984 |
| DE | 3 623 397 | 1/1988 |
| DE | 4 011 171 | 10/1991 |
| DE | 199 20 907 | 9/2000 |
| EP | 0 003 786 | 2/1979 |
| EP | 0 117 448 | 5/1984 |
| EP | 0158 499 | 10/1985 |
| EP | 168 769 | 1/1986 |
| EP | 0 273 531 | 7/1988 |
| EP | 336 368 | 1/1989 |
| EP | 0 490 667 | 6/1992 |
| EP | 0 559 046 | 8/1993 |
| EP | 0 569 592 | 11/1993 |
| EP | 0 589 446 | 3/1994 |
| FR | 5 734 M | 1/1968 |
| FR | 0 244 711 | 1/1968 |
| FR | 2 189 382 | 1/1974 |
| GB | 909098 | 10/1962 |
| JP | 1-45350 | 2/1989 |
| SE | 372 006 | 12/1974 |
| WO | WO 85/02404 | 6/1985 |
| WO | WO 85/03932 | 9/1985 |
| WO | WO 89/08643 | 3/1989 |
| WO | WO 93/15047 | 8/1993 |
| WO | WO 93/20099 | 10/1993 |
| WO | WO 95/19965 | 1/1995 |
| WO | WO 95/23609 | 9/1995 |
| WO | WO 96/12729 | 5/1996 |
| WO | WO 97/44312 | 11/1997 |
| WO | WO 98/07697 | 2/1998 |

OTHER PUBLICATIONS

Synth. Commun., 22 pp. 1547–1554 (1992).
J. Heterocycl. Chem., 30, pp. 1273–1277 (1993).
Synth. Commun., 27(8), pp. 1422–1431 (1997).
Monatsh. Chem., 107, 1413–1421 (1976).
J. Chem. Soc., 2294–2295 (1951).
J. Gen. Chem., USSR, (English Translation), 21, 1627–1631 (1951).
J. Am. Chem. Soc., 3870–3873 (1964).
J. Am. Chem. Soc., 88, 3162–3165 (1966).
Chem. Lett., 1529–1530 (1974).

(List continued on next page.)

Primary Examiner—Floyd D. Higel
Assistant Examiner—Golam M. M. Shameem
(74) Attorney, Agent, or Firm—Nixon & Vanderhye

(57) ABSTRACT

There is provided a process for the production of a compound of formula I,

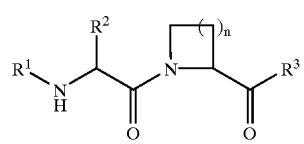

I which process comprises reaction of a compound of formula II,

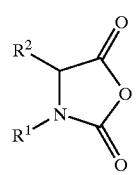

II with a compound of formula III,

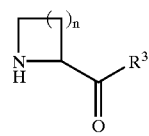

III wherein $R^1$, $R^2$, n and $R^3$ have meanings given in the description.

26 Claims, No Drawings

OTHER PUBLICATIONS

*J. Org. Chem.*, 40, 2697–2703 (1975).
*J. Org. Chem.*, 32, 3415–3425 (1967).
*J. Am. Chem. Soc.*, 93 2746–2755 (1971).
*Can J. Chem* 50, 299–303 (1972).
*Schyler's Z. Physiol. Chem.* 354, 267–285 (1973).
*Justus Liebigs Ann. Chem.*, 1263–1369 (1973).
*Justus Leibigs Ann. Chem.*, 1269–1275 (1973).
*J. Org. Chem.*, 30, 180–183 (1974).
*Chem. Lett.*, 1909–1910 (1994).
*Farmaco., Ed. Sci.*, 48 271–1277 (1993).
*Tetrahedron Lett.*, 36 807–810 (1995).
*Tetrahedron Lett.*, 36 1589–1592 (1995.

Federal Republic of Germany, German Patent Office, Patent Spec. DE 40 11 171 A1, C07C 229/06; Oct. 1991.

STN Int'l ; CAPLUS, AN; 1981:580859, *Phys. Chem.*, 1980; 26(3–4), sid 171–176.

STN Ind'l, CAOLD, AN; A55:544h.

Felfoldi et al.; "Preparation and Pharmacology of Cycloalkylaminopropyl Trimethoxybenzoates"; Chemistry of 1,3–Bifunctional Compounds, XXIV, 171–176, (1980).

COUPLING PROCESS

This application is 371 of PCT/SE01/00177 filed Jan. 30, 2001.

FIELD OF THE INVENTION

This invention relates to a novel process for the production of compounds comprising peptide linkages.

PRIOR ART

It is well known in the art that peptide linkages are typically formed via the coupling of an amine to a carboxylic acid.

Such coupling reactions are often carried out in the presence of so-called "coupling reagents", such as oxalyl chloride, EDC (1-(3-dimethylaminopropyl)-3-ethylcarbodiimide hydrochloride) DCC (dicyclohexylcarbodiimide), isobutyl chlorocarbonate, HBTU ([N,N,N',N'-tetramethyl-O-(benzotriazol-1-yl)uronium hexafluorophosphate]), HATU (O-(azabenzotriazol-1-yl)-N,N,N',N'-tetramethyluronium hexafluorophosphate) or TBTU ([N,N,N',N'-tetramethyl-O-(benzotriazol-1-yl)uronium tetrafluoroborate]), and an appropriate base.

Such agents, which are typically used to enhance the efficiency of the coupling reaction and/or the yield of the "coupled" product, have the disadvantage that they are expensive. Further, they may promote side-reactions and/or the formation of by-products, leading to a coupled product that has to be purified before it can be used, and/or to unacceptable levels of chemical effluent being released into the environment.

Thus, there is a need for an improved, cost-effective process for the formation of peptide linkages. Such a process should preferably minimise the number of reagents that need to be employed, and thus the number of side-reactions and by-products that are formed and need to be removed prior to further processing of the coupled product.

European patent applications EP 168 769 and EP 336 368, and U.S. Pat. No. 5,359,086 disclose the coupling of N-carboxyanhydrides (NCAs) to cyclic amino acids, such as proline and esters thereof. There is no mention in these documents of the coupling of NCAs to cyclic amino acid amides.

We have found, surprisingly, that peptide linkages may be formed by way of an efficient one-step process, in which NCAs are coupled directly to inter alia cyclic amino acid amide derivatives.

DESCRIPTION OF THE INVENTION

According to a first aspect of the invention there is provided a process for the production of a compound of formula I,

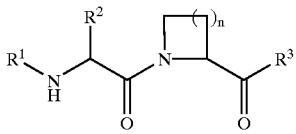

wherein
$R^1$ represents H or $C_{1-3}$ alkyl optionally substituted and/or terminated with one or more substituents selected from halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$;

$R^2$ represents $C_{1-8}$ alkyl, —$A^1$-$C_{4-8}$ cycloalkyl or —$A^1$-$C_{6-10}$ aryl, all of which are optionally substituted by one or more substituents selected from $C_{1-4}$ alkyl (which latter group is optionally substituted by one or more halo substituents), methylenedioxy, halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$;

$R^3$ represents $N(R^{12})R^{13}$ or $CH(R^{12})R^{13}$;

$R^{13}$ represents, at each occurrence, phenyl, $C_{1-3}$ alkylphenyl or $C(O)$phenyl, all of which groups are optionally substituted by one or more substituents selected from cyano, amidino, hydroxyamidino, halo, $C_{1-4}$ alkyl (which group is optionally substituted by one or more halo group), $SR^6$, $N(R^9)R^{10}$ or $OR^{11}$;

$R^9$ and $R^{10}$ independently represent, at each occurrence, H, $C_{1-4}$ alkyl or $C(O)R^{14}$;

$A^1$ represents, at each occurrence, a single bond or $C_{1-4}$ alkylene; n represents 1, 2 or 3;

$R^5$ represents, at each occurrence, H, $C_{1-6}$ alkyl or $C_{1-3}$ alkylphenyl, which latter group is optionally substituted by one or more substituents selected from $C_{1-4}$ alkyl (which latter group is optionally substituted by one or more halo substituents), methylenedioxy, halo, cyano, nitro, $S(O)_2NH_2$, $C(O)R^4$, $C(O)OR^{5a}$, $SR^6$, $S(O)R^7$, $S(O)_2R^8$, $N(R^9)R^{10}$ or $OR^{11}$; $R^4$, $R^{5a}$, $R^6$, $R^{11}$, $R^{12}$ and $R^{14}$ independently represent, at each occurrence, H or $C_{1-4}$ alkyl; and $R^7$ and $R^8$ independently represent, at each occurrence, $C_{1-4}$ alkyl, which process comprises reaction of a compound of formula II,

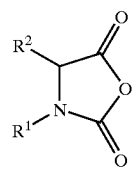

wherein $R^1$ and $R^2$ are as defined above, with a compound of formula III,

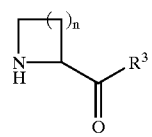

wherein $R^3$ and n are as defined above,
and which process is referred to hereinafter as "the process of the invention".

Alkyl groups that $R^1$, $R^2$, $R^4$, $R^5$, $R^{5a}$, $R^6$, $R^7$, $R^{8,}$ $R^9$, $R^{10}$, $R^{11,}$ $R^{12}$ and $R^{14}$ may represent, and with which $R^2$, $R^5$ and $R^{13}$ may be substituted, may be linear or, when there is a sufficient number (i.e. three) of carbon atoms, be branched and/or cyclic. Further, when there is a sufficient number (i.e. four) of carbon atoms, such alkyl groups may also be part cyclic/acyclic. Such alkyl groups may also be saturated or, when there is a sufficient number (i.e. two) of carbon atoms, be unsaturated and/or interrupted by oxygen.

For the avoidance of doubt, the point of attachment of alkylphenyl groups that $R^5$ and $R^{13}$ may represent is at the alkyl part of such groups. The alkyl part of such groups may be linear or, when there is a sufficient number (i.e. three) of carbon atoms, be branched. Such alkyl parts may also be saturated or, when there is a sufficient number (i.e. two) of carbon atoms, be unsaturated and/or interrupted by oxygen.

Alkylene chains that $A^1$ may represent may be linear or, when there is a sufficient number (i.e. two) of carbon atoms, be branched. Such chains may also be saturated or, when there is a sufficient number (i.e. two) of carbon atoms, be unsaturated and/or interrupted by oxygen.

As used herein, the term "halo" includes fluoro, chloro, bromo or iodo.

Preferred values of $R^1$ include $C_{1-3}$ alkyl groups (e.g. an ethyl or, particularly a methyl group) substituted and/or terminated by a $C(O)OR^5$ substituent, and, particularly, when the alkyl group is a $C_{2-3}$ alkyl group, those in which the optional $C(O)OR^5$ substituent is not located at the carbon atom to which the NH group is also attached. Preferred values of $R^5$ include H, linear or branched $C_{1-3}$ alkyl (e.g. iso-propyl or ethyl) or $C_{1-2}$ alkylphenyl (e.g. benzyl).

Preferred values of $R^2$ include —$A^1$-$C_{5-7}$ cycloalkyl or —Al-phenyl, in which, in both cases, $A^1$ represents a single bond or $C_{1-2}$ alkylene. Particularly preferred $R^2$ groups include cyclohexyl.

Preferred values of $R^3$ include $N(R^{12})R^{13}$, in which $R^{12}$ represents $C_{1-2}$ alkyl or, especially, H, and $R^{13}$ represents $C_{1-2}$ alkylphenyl (e.g. benzyl), which latter group is substituted with an amidino group, a hydroxyamidino group or, preferably, a cyano group, which substituent is preferably located at the 4-position on the phenyl part of that group (relative to the $C_{1-2}$ alkyl part). When $R^{13}$ represents an alkylphenyl group substituted at the phenyl part with amidino, hydroxyamidino or cyano, further such groups that may be mentioned include those that are also optionally substituted at the phenyl part with one or more halo (e.g. fluoro) atoms.

Preferred values of n include 2 and, especially, 1.

The process of the invention is preferably carried out in the presence of an appropriate base and a suitable solvent system, which solvent system may comprise aqueous and/or organic solvents. The base and solvent system that are employed should not react chemically with, or give rise to stereochemical changes in, the reactants or product once formed, or give rise to other side reactions.

Suitable bases include inorganic bases, such as hydroxides, alkoxides, hydrogen carbonates or carbonates of alkali metals (such as Na or K), or organic bases, such as common tertiary amine bases (e.g. triethylamine, diisopropylethylamine and N-methyl morpholine). Particularly preferred bases include amine bases.

Suitable aqueous solvents include water. Suitable organic solvents include acetates (e.g. ethyl acetate, iso-propyl acetate, butyl acetate), acetonitrile, toluene, dichloromethane, tetrahydrofuran, dimethylformamide and mixtures of any of these solvents.

It is preferred that water is present in the solvent system that is employed. We have found, advantageously, that, when water is employed as a solvent, the efficiency of the process is insensitive to the solid state properties of the amine of formula III that is employed.

NCA compounds of formula II are known in the art or may be prepared using conventional techniques (see, for example, the analogous processes described in German patent application DE 40 11 171 and international patent application WO 96/12729).

For example, compounds of formula II may be prepared by reaction of an amino acid compound of formula IV,

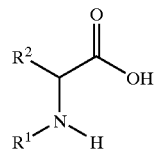

IV wherein $R^1$ and $R^2$ are as hereinbefore defined, with phosgene. This reaction may, for example, be carried out at elevated temperature (e.g. between 30° C. and reflux temperature) in the presence of a suitable solvent, such as tetrahydrofuran.

Compounds of formula IV, in which $R^1$ represents optionally substituted/terminated $C_{1-3}$ alkyl and which are optionally in the form of acid (e.g. hydrohalic acid) addition salts, may be prepared by reaction of a corresponding compound of formula IV in which $R^1$ is H, or an acid (e.g. a hydrohalic acid or an alkylsulphonic acid) addition salt thereof, with a compound of formula V,

  $R^{1a}$—$L^1$  V wherein $L^1$ represents a suitable leaving group (such as halo (e.g. Cl, Br or I), triflate, tosylate, mesylate, etc.) and $R^{1a}$ represents $C_{1-3}$ alkyl, optionally substituted and/or terminated with one or more substituents selected from halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$ and $R^4$, $R^5$, $R^6$, $R^7$, $R^8$, $R^9$, $R^{10}$ and $R^{11}$ are as hereinbefore defined. This reaction may, for example, be carried out at between room temperature and reflux temperature, in the presence of a suitable solvent system (e.g. aqueous and/or organic solvents (such as tetrahydrofuran, ethyl acetate, toluene, acetonitrile, etc.), including water/tetrahydrofuran mixtures and water/ethyl acetate mixtures), optionally in the presence of a base (e.g. an inorganic base, such as potassium hydrogen carbonate). The skilled person will appreciate that it may be desirable to protect the carboxylic acid group of the respective compound of formula IV with a suitable protecting group (e.g. a benzyl group) before carrying out this reaction.

Compounds of formula IV in which $R^1$ represents H and which are optionally in the form of acid (e.g. hydrohalic acid) addition salts may be prepared by hydrolysis of a corresponding compound of formula II in which $R^1$ represents H under appropriate reaction conditions. The skilled person will appreciate that it may be possible and/or desirable to protect the carboxylic acid group of the resultant compound of formula IV with a suitable protecting group (e.g. a benzyl group) by performing this hydrolysis in the presence of a suitable protecting reagent (e.g. benzyl alcohol).

Alternatively, compounds of formula IV in which $R^1$ represents $C^{1-3}$ alkyl substituted or terminated by $C(O)OR^5$, provided that, in the case of a $C_{2-3}$ alkyl group, the $C(O)OR^5$ group is not located at the carbon atom to which the NH group is also attached, may be prepared by hydrogenation of a corresponding compound of formula IV in which $R^1$ represents H in the presence of either a compound of formula VI,

or a compound of formula VII,

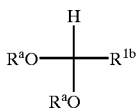

in which, in both cases, $R^{1b}$ represents $C(O)OR^5$ or $C_{1-2}$ alkyl substituted or terminated by $C(O)OR^5$ and $R^5$ is as hereinbefore defined, and, in the case of a compound of formula VII, the $R^a$ groups either represent, separately, C 1-4 alkyl groups, or are joined together to form a $C_{2-4}$ alkylene chain, under appropriate reaction conditions. Reaction of a compound of formula IV in which $R^1$ is H with a compound of formula VI, or a compound of formula VII, may, for example, be carried out in the presence of a suitable solvent system (e.g. an alkyl alcohol (such as methanol, ethanol, i-propanol or n-propanol), which alcohol should be selected to avoid trans-esterification reactions in the reactants or products of the relevant reaction) and, optionally, an appropriate acid, such as an inorganic acid (e.g. HCl) or an organic acid (e.g. methanesulphonic acid, toluenesulphonic acid etc). The skilled person will appreciate that these reactions may be carried out at around room temperature or above (e.g. up to the reflux temperature of the solvent that is employed (e.g. at around 40 to 60° C., such as about 50° C.)), under hydrogen, for example under a positive pressure of hydrogen (e.g. 3 to 8 (e.g. 4 to 6, such as 5)) atmospheres, and in the presence of an appropriate hydrogenation catalyst system (e.g. Pd/C, Pt/C). The skilled person will appreciate that altering the pressure of hydrogen during the relevant reaction will alter the reflux temperature of the solvent.

According to two further aspects of the invention, there is thus provided a process for the preparation of a compound of formula IV in which $R^1$ represents $C_{1-3}$ alkyl substituted or terminated by $C(O)OR^5$ provided that, in the case of a $C_{2-3}$ alkyl group, the $C(O)OR^5$ group is not located at the carbon atom to which the NH group is also attached, which process comprises hydrogenation of a corresponding compound of formula IV in which $R^1$ represents H in the presence of a compound of formula VI as hereinbefore defined, or a compound of formula VII as hereinbefore defined.

These processes for the preparation of compounds of formula IV in which $R^1$ represents $C_{1-3}$ alkyl substituted or terminated by $C(O)OR^5$ may have the advantage that such compounds may be prepared in fewer steps than other processes for the preparation of equivalent compounds of formula IV, which other processes are either described herein or may be described elsewhere in the prior art. In particular, this process avoids the need for protection of the relevant carboxylic acid group in a compound of formula IV in which $R^1$ represents H prior to coupling with e.g. a compound of formula V, for example as described herein.

Compounds of formula III, V, VI and VII are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other substituents using techniques well known to those skilled in the art. For example, amino may be converted to amido, amido may be hydrolysed to amino, hydroxy may be converted to alkoxy, alkoxy may be hydrolysed to hydroxy, and, where appropriate, cyano may be converted to amidino or hydroxyamidino.

It will be appreciated by those skilled in the art that, in the processes described above, the functional groups of intermediate compounds may be, or may need to be, protected by protecting groups. In particular, it may be desirable to protect the carboxylic acid functionality of a compound of formula IV (and acid addition salts thereof), with an appropriate protecting group (e.g. a benzyl group), which should be removed before reaction with phosgene.

Functional groups which it is desirable to protect thus include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl, benzyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxycarbonyl. Suitable protecting groups for carboxylic acid include $C_{1-6}$ alkyl, ally or benzyl esters.

The protection and deportation of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", $3^{rd}$ edition, T W Greene & P G M Wutz, Wiley-Interscience (1999).

Compounds of formula I prepared by way of the process of the invention may be utilised in a subsequent peptide coupling reaction and/or may be converted to other compounds of formula I. For example, compounds of formula I wherein $R^3$ represents $N(R^{12})R^{13}$, in which $R^{13}$ represents phenyl, C(O)phenyl, or, preferably, $C_{1-3}$ alkylphenyl (e.g. benzyl) substituted (at the respective phenyl parts) by cyano (e.g., in the case of $C_{1-3}$ alkylphenyl, at the 4-position relative to the $C_{1-3}$ alkyl part) may be converted to equivalent compounds of formula I in which the relevant phenyl group is substituted by an amidino, or, preferably, a hydroxyamidino, group under techniques known to those skilled in the art (e.g. using hydroxylamine).

The process of the invention is thus useful in the production of chemical compounds comprising peptide linkages and, in particular, peptide compounds comprising cyclic amino acid groups.

The process of the invention possesses the surprising advantage that peptide compounds of formula I may be obtained efficiently from readily-available starting materials without the need for the employment of coupling agents.

Further, the process of the invention may have the advantage that compounds of formula I may be prepared in higher yields, in less time, more conveniently, and at a lower cost, than when prepared in processes described in the prior art.

The invention is illustrated, but in no way limited, by the following examples.

EXAMPLE 1

Ethyl 2-[((1R)-2-{(2S)-2-[({4-cyanobenzyl }-amino) carbonyl]azetidinyl}-1-cyclohexyl-2-oxoethyl)amino] acetate (a) Benzyl (2R)-2-amino-2-cyclohexylethanoate methanesulfonate To a suspension of (2R)-2-amino-2-cyclohexylethanoic acid (200 g, 1.27 mol) and benzyl alcohol (276 g, 2.54 mol) in toluene (1600 mL) was added methanesulphonic acid at a rate which did not allow the temperature to reach 100° C. The reaction was stirred for an additional six hours at between 110 and 115° C. The water that was produced was distilled off using a Dean-Stark trap. An additional portion of benzyl alcohol (276 g, 2.54 mol) was added and the mixture was refluxed for a further twelve hours with water distillation. The reaction mixture was then cooled and methyl tert-butyl ether was added to initiate crystallisation. The product was filtered and dried to yield 404 g (92%) of the sub-title compound.

(b) Benzyl (2R)-2-cyclohexyl-2-[(2-ethoxy-2-oxoethyl) amino]ethanoate hydrochloride To a suspension of $KHCO_3$ (222 g, 2.22 mol) in water was added benzyl (2R)-2-amino-2-cyclohexylethanoate methanesulfonate (200 g, 0.58 mol, from step (a) above) in portions. After charging was completed, the mixture was stirred for 15 minutes at 20 to 25° C. The mixture was then diluted with tetrahydrofuran (150 mL) under continuous stirring for 30 minutes. Ethyl bromoacetate was added over one hour, whereupon the mixture was stirred for eight hours at 35° C. The temperature was then raised to 50° C. and reacted for an additional four hours. The reaction mixture was cooled to ambient temperature and then diluted with toluene (450 mL). The two phases were separated and the organic phase was washed with water twice, reduced, filtered and the product isolated as its hydrochloride salt, using hydrochloric acid in heptane. After drying, 199 g (93%) of the sub-title compound was obtained.

(c) (2R)-2-Cyclohexyl-2-[(2-ethoxy-2-oxoethyl)amino] ethanoic acid (Alternative A)

Benzyl (2R)-2-cyclohexyl-2-[(2-ethoxy-2-oxoethyl) amino]ethanoate hydrochloride (40 g, 0.1 mol, from step (b) above) dissolved in iso-propyl alcohol (320 mL) was hydrogenated in the presence of 5% Pd/C (2 g, 50% aq.) for 3 h at 30° C. After removal of the catalyst by filtration, the filtrate was neutralised with tetrabutylammonium hydroxide and the pH was adjusted to 5.2. To rid the resultant of water, the suspension was evaporated and washed repeatedly with iso-propylalcohol and dried to yield 49 g (94%) of the sub-title compound.

(Alternative B)

Ethylglyoxalate (50% in toluene; 71.5 g) was added to a mixture of (2R)-2-amino-2-cyclohexylethanoic acid (10 g; 64 mmol) and methanesulphonic acid (4.9 g; 0.51 mol) in ethanol (100 mL). The mixture was hydrogenated in the presence of 0.5 g of 5% Pd/C under a pressure of 5 atm. for 6 hours at 22° C. The mixture was then warmed to 50° C. and hydrogenation was continued for an additional 14 hours. The catalyst was removed by filtration and the pH was adjusted to a value of between 4 and 5. Water (200 mL) was added to the resultant gelatinous slurry and the solid was filtered, washed and dried, giving 9.4 g (50%) of the sub-title compound as a white powder.

$^1$H NMR ($D_2O$) δ 1.29 (t), ca. 1.1–1.4 (m), ca. 1.6–1.9 (m), ca. 2.0–2.2 (m), 4.04 (d), 4.08 (q), 4.31 (q)

$^{13}$C NMR ($D_2O$)δ13.9, 25.9, 26.1, 26.3, 28.5, 29.0, 39.4, 47.6, 64.4, 66.1, 167.7, 170.9

(d) Ethyl 2-[(4R)-4-cyclohexyl-2,5-dioxo-1,3-oxazolidin-3-yl]acetate

Phosgene (28.9 kg, 291.9 mol) was added to (2R)-2-cyclohexyl-2-[(2-ethoxy-2-oxoethyl) amino]ethanoic acid (44.2 kg, 182 mol, obtained analogously to the method described in step (c) (Alternative A) above) in tetrahydrofuran (340 kg) at 40° C. over one hour. The reaction was deemed to be complete after a further hour. The mixture was concentrated at reduced pressure. The residue was diluted with tetrahydrofuran (272.6 kg) and the pH was adjusted at 0° C. to 6.5 with N-methylmorpholine (15.3 kg). The reaction was continued for a further 45 minutes. HCl/dioxane (0.34 kg) was then added and the residue was filtered through Celite®. The filter cake was washed twice with tetrahydrofuran. The combined filtrates were concentrated at reduced pressure at 20° C. To the residue was added heptane (250 kg), and the mixture was concentrated again. To the resultant residue further heptane (81 kg) was added. The temperature was adjusted to 0° C. and the mixture was allowed to crystallise for five hours. The crystals were filtered, washed (3×30 kg heptane) and dried (low pressure, 20° C.), to yield 46 kg (95%) of the sub-title compound.

$^{13}$C NMR:δ168.2, 167.9, 152.3, 65.3, 61.2, 43.8, 37.5, 27.3, 26.0, 25.6, 25.2, 13.9

(e) Ethyl 2-[((1R)-2-{(2S)-[({4-cyanobenzyl}amino) carbonyl]azetidinynl}-1-cyclohexyl-2-oxoethyl)amino] acetate 4-Methylmorpholine (4.9 g, 48.6 mmol) was added at 30° C. to a mixture of (2S)-N-(4-cyanobenzyl)-2-azetidinecarboxamide (10.8 g, 43.9 mmol, prepared analogously to methods described generally in international patent applications WO 94/29336, WO 99/64391 and WO 00/12473) and ethyl 2-[(4R)-4-cyclohexyl-2,5-dioxo-1,3-oxazolidin-3-yl]acetate (11.6 g, 42.2 mmol, see step (d) above) in ethyl acetate (28 mL). After five minutes of agitation, sodium chloride (aq., 9.3 mL, 10% w/w and 0.066% EDTA) was added. After an additional three hours of agitation, the organic layer containing the title compound was separated, yielding 99% of the desired compound.

$^{13}$C NMR ($CDCl_3$): δ14.3, 19.2, 26.1, 26.2, 26.4, 29.2, 30.0, 41.1, 42.9, 48.6, 49.5, 61.0, 62.0, 62.8, 111.1, 118.9, 128.1×2, 132.5×2, 144.1, 171.1, 172.4, 175.7

EXAMPLE 2

Ethyl 2-({(1R)-1-cyclohexyl-2-oxo-2-[(2S)-2-(2-phenylacetyl)azetidinyl]-ethyl}amino)acetate To a solution of 1-[(S)-azetidinyl]-2-phenyl-1-ethanone hydrochloride (9 g, 20 mmol) and ethyl 2-[(4R)-4-cyclohexyl-2,5-dioxo-1,3-oxazolidin-3-yl] acetate (6.7 g, 25 mmol, see Example 1(d) above) in ethyl acetate (50 mL) was added N-methyl morpholine (4 mL, 40 mmol). When the reaction was deemed to be complete according to HPLC, the reaction was worked up by extractions. Concentration gave 7 g of the title compound as an oil (84%).

LC–MS:(m+1) 417 (m/z)

EXAMPLE 3

Ethyl 2-[((1S)-2-{(2R)-2-[({4-[{[(benzyloxy)carbonyl] amino}(hydroxyimino)methyl] benzyl}amino)carbonyl] azetidinyl }-1-cyclohexyl-2-oxoethyl)amino] acetate To a solution of benzyl [4-({[(2S)azetidinylcarbonyl] amino}methyl)-phenyl] (hydroxyimino)methylcarbamate hydrochloride (11.7 g, 25 mmol) and ethyl 2-[(4R)-4-cyclohexyl-2,5-dioxo-1,3-oxazolidin-3-yl]acetate (6.7 g, 25 mmol, see Example 1(d) above) in tetrahydrofuran (55 mL) was added N-methyl morpholine (5 mL, 50 mmol). When the reaction was deemed to be complete according to HPLC, the reaction was filtered and worked up by extractions. Drying and concentration gave the desired compound as an oil (77%).

LC–MS:(m+1)=608 (m/z)

EXAMPLE 4

The following compound was prepared using analogous techniques to those described herein:

ethyl 2-[((1R)-2-{(2S)-2-[({4-[amino(hydroxyimino) methyl]benzyl}amino)-carbonyl] azetidinyl}-1-cyclohexyl-2-oxoethyl)amino]acetate di(trifluoromethanesulfonate).

What is claimed is:

1. A process for the production of a compound of formula I,

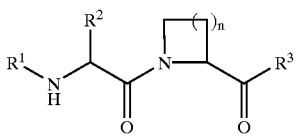

I wherein $R^1$ represents H or $C_{1-3}$ alkyl optionally substituted or terminated with one or more substituents selected from halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$;

$R^2$ represents $C_{1-8}$ alkyl, $-A^1-C_{4-8}$ cycloalkyl or $-A^1-C_{6-10}$ aryl, all of which are optionally substituted by one or more substituents selected from $C_{1-4}$ alkyl (which latter group is optionally substituted by one or more halo substituents), methylenedioxy, halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$;

$R^3$ represents $N(R^{12})R^{13}$ or $CH(R^{12})R^{13}$;

$R^{13}$ represents, at each occurrence, phenyl, $C_{1-3}$ alkylphenyl or C(O)phenyl, all of which groups are optionally substituted by one or more substituents selected from cyano, amidino, hydroxyamidino, halo, $C_{1-4}$ alkyl (which group is optionally substituted by one or more halo group), $SR^6$, $N(R^9)R^{10}$ or $OR^1$;

$R^9$ and $R^{10}$ independently represent, at each occurrence, H, $C_{1-4}$ alkyl or $C(O)R^{14}$;

$A^1$ represents, at each occurrence, a single bond or $C_{1-4}$ alkylene;

n represents 1, 2 or 3;

$R^5$ represents, at each occurrence, H, $C_{1-6}$ alkyl or $C_{1-3}$ alkylphenyl, which latter group is optionally substituted by one or more substituents selected from $C_{1-4}$ alkyl (which latter group is optionally substituted by one or more halo substituents), methylenedioxy, halo, cyano, nitro. $S(O)_2NH_2$, $C(O)R^4$, $C(O)OR^{5a}$, $SR^6$, $S(O)R^7$, $S(O)_2R^8$, $N(R^9)R^{10}$ or $OR^{11}$;

$R^4, R^{5a}, R^6, R^{11}, R^{12}$ and $R^{14}$ independently represent, at each occurrence, H or $C_{1-4}$ alkyl; and $R^7$ and $R^8$ independently represent, at each occurrence, $C_{1-4}$ alkyl, which process comprises reaction of a compound of formula II,

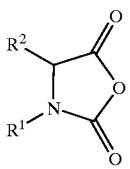

II wherein $R^1$ and $R^2$ are as defined above, with a compound of formula III,

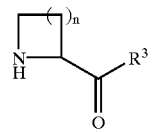

III wherein $R^3$ and n are as defined above.

2. A process as claimed in claim 1, wherein $R^1$ represents $C_{1-3}$ alkyl substituted or terminated by a $C(O)OR^5$ substituent.

3. A process as claimed in claim 2, wherein the $C_{1-3}$ alkyl group is a methyl group or an ethyl group.

4. A process as claimed in claim 1 wherein $R^5$ represents H, linear or branched $C_{1-3}$ alkyl or $C_{1-2}$ alkylphenyl.

5. A process as claimed in claim 4 wherein $R^5$ represents iso-propyl, ethyl or benzyl.

6. A process as claimed in claim 1 wherein $R^2$ represents $-A^1-C_{5-7}$ cycloalkyl or $-A^1$-phenyl, in which, in both cases, $A^1$ represents a single bond or $C_{1-2}$ alkylene.

7. A process as claimed in claim 1 wherein $R^3$ represents $N(R^{12})R^{13}$, in which $R^{12}$ represents H or $C_{1-2}$ alkyl and $R^{13}$ represents $C_{1-2}$ alkylphenyl, which latter group is substituted with an amidino group, a hydroxyamidino group or a cyano group.

8. A process as claimed in claim 7, wherein the substituent is located at the 4-position of the phenyl part of the $C_{1-2}$ alkylphenyl group (relative to the $C_{1-2}$ alkyl part).

9. A process as claimed in claim 1 wherein the process is carried out in the presence of a base.

10. A process as claimed in claim 9, wherein the base is a tertiary amine base.

11. A process as claimed in claim 10, wherein the base is triethylamine, diisopropylethylamine or N-methyl morpholine.

12. A process as claimed in claim 1 wherein the reaction is carried out in the presence of a solvent system that includes water.

13. A process as claimed in claim 1, wherein the reaction is carried out in the presence of an organic solvent, which is selected from an acetate, acetonitrile, toluene, dichloromethane, tetrahydrofuran, dimethylformamide or a mixture of any of these solvents.

14. A process as claimed in claim 1 wherein the compound of formula II is prepared by reaction of a compound of formula IV,

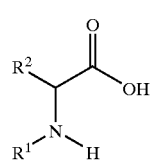

IV where $R^1$ and $R^2$ are as defined in claim 1 with phosgene.

15. A process as claimed in claim 14, wherein, in the compound of formula IV, $R^1$ represents optionally substituted/terminated $C_{1-3}$ alkyl, the compound is optionally in the form of an acid addition salt, and the compound of formula IV is prepared by reaction of a corresponding compound of formula IV in which $R^1$ is H, or an acid addition salt thereof, with a compound of formula V, $$R^{1a}-L^1$$

V wherein $L^1$ represents a leaving group and $R^{1a}$ represents $C_{1-3}$ alkyl, optionally substituted and/or terminated with one or more substituents selected from halo, cyano, nitro, $S(O)_2NH_2$, $C(O)R^4$, $C(O)OR^5$, $SR^6$, $S(O)R^7$, $S(O)_2R^8$, $N(R^9)R^{10}$ or $OR^{11}$ and $R^4$, $R^5$, $R^6$, $R^7$, $R^8$, $R^9$, $R^{10}$ and $R^{11}$ are as defined in claim 1.

16. A process as claimed in claim 14, wherein in the compound of formula IV, $R^1$ represents H, the compound is optionally in the form of an acid addition salt, and the compound of formula IV is prepared by hydrolysis of a corresponding compound of formula II, as defined in claim 1, in which $R^1$ represents H.

17. A process as claimed in claim 14, wherein, in the compound of formula IV, $R^1$ represents $C_{1-3}$ alkyl substituted or terminated by $C(O)OR^5$, provided that, in the case of a $C_{2-3}$ alkyl group, the $C(O)OR^5$ group is not located at the carbon atom to which the NH group is also attached, and the compound of formula IV is prepared by hydrogenation of a corresponding compound of formula IV in which $R^1$ represents H in the presence of a compound of formula VI,

  VI in which $R^{1b}$ represents $C(O)OR^5$ or $C_{1-2}$ alkyl substituted or terminated by $C(O)OR^5$ and $R^5$ is as defined in claim 1.

18. A process as claimed in claim 14, wherein, in the compound of formula IV, $R^1$ represents $C_{1-3}$ alkyl substituted or terminated by $C(O)OR^5$, provided that, in the case of a $C_{2-3}$ alkyl group, the $C(O)OR^5$ group is not located at the carbon atom to which the NH group is also attached, and the compound of formula IV is prepared by hydrogenation of a corresponding compound of formula IV in which $R^1$ represents H in the presence of a compound of formula VII,

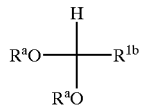  VII in which $R^{1b}$ is as defined in claim 17 and the $R^a$ groups either represent, separately, $C_{1-4}$ alkyl groups, or are joined together to form a $C_{2-4}$ alkylene chain.

19. A process for the preparation of a compound of formula IV as defined in claim 14, in which $R^1$ represents $C_{1-3}$ alkyl substituted or terminated by $C(O)OR^5$, provided that, in the case of a $C_{2-3}$ alkyl group, the $C(O)OR^5$ group is not located at the carbon atom to which the NH group is also attached, which process comprises hydrogenation of a corresponding compound of formula IV in which $R^1$ represents H in the presence of a compound of formula VI as defined above.

20. A process for the preparation of a compound of formula IV as defined in claim 14, in which $R^1$ represents $C_{1-3}$ alkyl substituted or terminated by $C(O)OR^5$, provided that, in the case of a $C_{2-3}$ alkyl group. the $C(O)OR^5$ group is not located at the carbon atom to which the NH group is also attached, which process comprises hydrogenation of a corresponding compound of formula IV in which $R^1$ represents H in the presence of a compound of formula VII as defined above.

21. A process as claimed in claim 17, wherein, in the process step for the production of the compound of formula IV, the reaction is carried out in the presence of ethanol as solvent.

22. A process as claimed in claim 17, wherein, in the process step for the production of the compound of formula IV, the reaction is carried out in the presence of an acid.

23. A process as claimed in claim 22, wherein the acid is methanesulphonic acid.

24. A process as claimed in claim 17, wherein, in the process step for the production of the compound of formula IV, the reaction is carried out in the presence of a Pd/C or a Pt/C catalyst.

25. A process for the preparation of a compound of formula I wherein $R^3$ represents $N(R^{12})R^{13}$, in which $R^{12}$ is as defined in claim 1 and $R^{13}$ represents phenyl, C(O)phenyl or $C_{1-3}$ alkylphenyl, each of which are substituted by a hydroxyamidino group, which process comprises a process as defined above, in which, in the compound of formula III, $R^3$ represents $N(R^{12})R^{13}$, in which $R^{12}$ is as defined in claim 1 and $R^{13}$ represents phenyl, C(O)phenyl or $C_{1-3}$ alkylphenyl, each of which are substituted by a cyano group, followed by reaction of the resultant compound of formula I with hydroxylamine.

26. A compound of formula II as defined in in claim 2.

* * * * *